United States Patent [19]

Palladino

[11] Patent Number: 4,714,674

[45] Date of Patent: Dec. 22, 1987

[54] CHEMOTACTIC ASSAY FOR IMMUNOGENICITY

[75] Inventor: Michael A. Palladino, San Mateo, Calif.

[73] Assignee: Genentech, Inc., San Francisco, Calif.

[21] Appl. No.: 707,005

[22] Filed: Feb. 28, 1985

[51] Int. Cl.⁴ .................. A61K 39/00; C12Q 1/02; C12Q 1/34; G01N 33/531
[52] U.S. Cl. .................................. 435/18; 424/88; 435/29; 435/68; 435/172.3; 436/503; 436/543; 436/547; 935/60; 935/65
[58] Field of Search ............... 436/503, 547, 543; 435/29, 18, 68, 172.3; 424/88; 935/60, 65

[56] References Cited

PUBLICATIONS

J. T. Bennett et al, *FEBS Letters* 116, 57–61, 1980.
J. D. Watson et al, *Recombinant DNA*, Scientific American Books, New York, 1983, p. 236.

*Primary Examiner*—Sidney Marantz
*Assistant Examiner*—David A. Saunders

[57] ABSTRACT

The in vitro chemotactic activity of recombinant protein compositions is a predictive test for in vivo immunogenicity. Recombinant synthesis methods and subsequent purification or processing techniques are modified in the light of the chemotactic assay results in order to reduce or enhance the in vivo immunogenicity of the compositions. The invention ameliorates a major cost and source of uncertainty in the development of recombinant protein compositions. Immunogenicity of substances in vivo is modulated by binding chemotactic polypeptides thereto.

25 Claims, No Drawings

CHEMOTACTIC ASSAY FOR IMMUNOGENICITY

BACKGROUND

This invention relates to assays for determining the character of compositions containing heterologous proteins or polypeptides made by recombinant cells. More particularly, this invention is concerned with aiding in predicting the likelihood that a recombinant product will be immunogenic in animal recipients.

It now is known that certain recombinantly-prepared proteins, e.g. human growth hormone (hereinafter hGH) or alpha interferon (α-IFN) are capable of raising or inducing antibodies in recipients that cross-react with the same protein from nonrecombinant sources. For example, see P. Trown et al., "The Lancet" Jan. 15, 1983: 81–84. It has been speculated that such immunogenicity is the result of aberrant folding of the recombinant protein, protein modifications or denaturation during purification, or the presence of different or extra amino acid residues in the sequence of the recombinant protein. While the immunogenicity of recombinant proteins remains unassociated with adverse clinical consequences in recipient patients, it would be desirable to be able to assay candidate therapeutic compositions for potential immunogenicity in animals. At the present time the only technique available for assessing immunogenicity in humans is to administer the candidate compositions to primates and assay the test animal sera over a period of months to determine whether or not the composition is immunogenic. Not only is this quite expensive, as primate colonies in the United States are limited and in high demand for scientific studies, but considerable time is needed to detect an immunogenic response. Further, so few animals typically are available that it is difficult to assemble a sufficient amount of data.

One of the purposes of immunogenicity studies is to evaluate alternative purification or preparation methodologies for therapeutic proteins. For example, it might be desired to synthesize a recombinant protein as an amino acid sequence variant in which an additional N-terminal methionyl residue is present. Such variants generally result from direct recombinant expression of a protein not having a host-recognized signal sequence. The progress of research will be greatly retarded if clinical trials are needed to evaluate such variants to determine if they are immunogenic. Therefore a significant need exists in the art for an inexpensive and rapid assay that will provide at least some indication as to the likely immunogenicity in humans or other animals of a candidate recombinant product.

On the other hand, it may be desirable to prepare a protein in recombinant culture that is capable of raising antibodies which will cross-react with the protein as it is found in nature. Such recombinant proteins typically are fusions of bacterial proteins with mammalian proteins against which it is desired to stimulate an immune response. The antibodies so produced are useful, for example, in diagnostic assays. The search for highly immunogenic proteins is essentially random. A method is needed for identifying classes of such proteins without the need for in vivo immunization studies.

SUMMARY

I have discovered that the leukocyte chemotaxis of recombinant products exhibits a substantial correlation with their immunogenicity and accordingly serves as a useful in vitro predictive assay for this property in vivo.

The method herein comprises contacting leukocytes with a candidate composition comprising a protein synthesized in recombinant culture and observing for chemotactic effect of the candidate composition. The degree of in vivo immunogenicity of the composition is a direct function of its chemoattractive character for leukocytes. The assay results are useful for identifying modifications in the methods for manufacture of the recombinant proteins which are either less or more immunogenic, depending upon the desired uses for the recombinant protein.

The less immunogenic recombinant proteins so identified are useful for therapies where the incidental generation of antibodies against the recombinant protein is not desired, i.e., where the recombinant protein itself is the therapeutic agent. This is the situation with administration of human growth hormone to hypopituitary dwarfs.

On the other hand, enhanced immunogenicity is a useful property where it is desired to raise antibodies against a recombinant protein where the antibodies are a desired therapeutic or diagnostic composition.

As a corollary to my discovery that in vivo immunogenicity is correlated to chemotaxis, this invention provides methods for the preparation of highly immunogenic conjugates or fusions of the protein against which it is desired to raise antibodies, i.e. the target protein. Chemotactic polypeptides are expressed in recombinant culture as N-terminal fusions with target proteins or are conjugated to the target proteins. Such conjugates are useful, for example, as vaccines for providing immunity against infective agents or for stimulating the generation of antibodies where the target proteins are only weakly immunogenic.

DETAILED DESCRIPTION

Numerous assay systems for determining the chemotaxis of substances are known. Principally, the methods comprise creating a concentration gradient of the substance to be tested, introducing suitable living leukocytes into the gradient at the lower concentrations of the substance and observing the amoeboid migration of the leukocytes towards the regions of the gradient having relatively higher concentrations of the substance. Suitable chemotactic assays generally involve the microscopic observation of leukocyte migration through microporous filters or membranes across which a concentration gradient is established (S. Boyden, 1962, "J. Exp. Med." 115: 453; L. Harvath et al., 1980, "J. Immunol. Meth." 37: 39; G. Grimes et al., "Exp. Cell Res." 79: 375; (1973) and R. Carpenter, 1963, "J. Immunol." 91: 803). Other in vivo or in vitro assays which correlate with in vivo leukocyte migration are included within the scope herein. The chemotactic response of neutrophils is initiated by the binding of chemoattractant to cell surface receptor. At certain concentrations chemoattractants stimulate production of superoxide anion ($O_2-$) and secretion of lysosomal enzymes such as N-acetyl-B-D-glucosaminidase (W. Marasco et al., 1984, "J. Biol. Chem." 259(9): 5430–5439). Accordingly, it may be more convenient to determine superoxide anion or lysosomal enzymes in neutrophil culture supernatants after exposure to test compositions.

The leukocytes which are used in the assay herein are any migratory-capable immune cell type such as leukocytes particularly including granulocytes also known as neutrophils. They are obtained by known methods from the blood of healthy donors. It is not necessary that they be recovered from the same individuals to be treated with the candidate composition, but instead are simply selected from the population as a whole. They should be selected from animals of the species to which the candidate recombinant composition is to be administered. This species may or may not be the species of origin of the protein being made in recombinant culture and included in the candidate composition.

The candidate recombinant compositions to be assayed are produced by cells which have been transformed to express a protein ordinarily not produced by the cell, or not produced by the cell in the amounts obtained upon transformation. Incidently, for convenience the term protein shall be considered to include polypeptides having small molecular weights, on the order of 10-20 residue or greater up to the size ordinarily ascribed to proteins. Transformed cells are cells that have taken up exogenous nucleic acids which affect the character of the cell. Ordinarily the exogenous nucleic acids will encode a protein which is foreign or heterologous to the cell being transformed, such cells being called host cells. Typical host cells include bacteria such as *E. coli* or bacillus, yeast or vertebrate (ordinarily mammalian) cells.

It is not necessary to purify the compositions containing recombinant proteins prior to conducting the chemotaxis assay. Preferably, however, the compositions will be purified free of insoluble matter from host cells and known undesirable substances, e.g., endotoxin in the case of gram negative bacterial hosts. It should be noted, however, that an object herein is to enable screening for those purification procedures which separate potentially immunogenic proteins from the desired protein. Accordingly, the candidate compositions often will be drawn from a bank of preparations purified by different processes. Similarly, candidate compositions may represent a bank of variant or mutated proteins, or a bank of proteins from cells or proteins processed in various ways that do not involve purification, e.g. treatment of the recombinant cells with different or variant killing techniques prior to recombinant protein harvest or later treatment of the protein to modify or preserve its activity, e.g. by lyophilization. Together, such variations in the method for making the recombinant protein composition are termed recombinant cell protein transformation or processing parameters.

The concentration of protein in the composition should be adjusted to represent approximately the molar dose expected to be found in blood plasma upon administration to recipients. This obviously will vary greatly depending on the protein, its therapeutic utility and its route of administration. The protein concentration of the composition to be tested in the assay ordinarilly will range about from $10^{-4}$ to $10^{-10}$M, usually $10^{-5}$ to $10^{-8}$M.

The degree of chemotaxis is expressed in different units depending upon the assay method employed, but generally the result with such assays is expressed in terms of the number of leukocytes found to have migrated to a certain location in the test composition concentration gradient. The absolute number is not instructive. What is relevant is the number found in relation to positive and negative controls. Typically, the positive control will be formyl-methionyl-leucyl-phenylalanine (W. Marasco et al., 1984, "J. Biol. Chem." 259(9): 5430) and the negative control will be Hank's balanced salt solution, a commercially available leukocyte medium. Candidate compositions should be considered immunogenic which induce chemotaxis at greater than about 10 percent of that which is induced by the same concentration of formyl-methionyl-leucyl-phenylalanine (henceforth designated FMLP) so long as that is greater than the negative control. At present, known immunogenic recombinant preparations have shown chemotactic activities ranging about from about 45 percent to about 80 percent of FMLP in the same concentration, but it is conceivable that preparations will be encountered which are greater or less immunogenic. However, compositions that are less chemotactic than 10 percent of FMLP activity or in the range of the negative control should be considered acceptable for therapeutic use.

When a composition is determined to be chemotactic, steps are taken to modify the recombinant cell protein transformation or processing parameters in an effort to reduce or enhance the chemotactic character of the composition. Preferably the parameters first modified will be processing parameters since such changes do not entail modifying the amino acid sequence of the protein. These generally will be parameters controlling the purification of the desired protein. For example, additional purification steps may be introduced in order to remove or retain potential chemotactic factors or certain steps may be deleted or retained that are thought to be the source of the chemotactic property. Alternatively, potential protein denaturing steps such as heat killing the recombinant cells or lyophilizing the composition may be substituted by other procedures. Also, host cells may be selected on the basis of which host yields compositions having the least or greatest chemotactic effect. Finally, if these efforts fail then it may be necessary to modify the amino acid sequence of the recombinant.

The purpose of this method is to identify potentially immunogenic compositions. Based on this knowledge, the artisan is directed to make changes in the composition or its method of manufacture. These changes, however, are myriad and can be expected to evolve in the future along with progress in recombinant and purification technology.

Having made changes in the protein transformation or processing parameters, the resulting compositions are once again assayed for chemotaxis. Those which show improvement are selected for commercial manufacture or for further development.

Where it is desired to reduce the chemotactic properties of the composition the protein may be expressed as a signal sequence fusion that is processed by the host cells to the mature protein (without an extraneous amino-terminal methionyl). Alternatively where a more immunogenic protein is desired DNA encoding the protein of interest is ligated to DNA encoding a bacterial protein or polypeptide such as β-galactosidase.

The immunogenic conjugates herein are covalent conjugates of the target substance with chemotactic polypeptides, including amino-terminal recombinant fusions, or adsorption complexes of the polypeptides and target substance. The target substance is that against which it is desired to raise antibodies. Fusions are produced by providing DNA encoding a target protein, DNA encoding a chemotactic polypeptide inserted into the DNA in place of the first N-terminal amino acid of the mature target protein, and expressing the DNA which encodes the fusion in a recombinant host. The DNA encoding the chemotactic polypeptide is inserted in place of the first amino acid codon for the target protein by site directed mutagenesis or by ligating a synthetic DNA segment encoding the polypeptide and, optionally, a portion of the target protein gene into the gene at convenient restriction enzyme sites flanking the first codon. As examples of these methods see J. Adelman et al., 1983, "DNA" 2(3): 183–193; A. Hui, 1984, "EMBO Journal" 3(3): 623–629; U.K. patent application 2,130,219A; G. Winter et al., 1982, "Nature" 299: 756–758; and R. Wallace et al., 1981, "Nucleic Acids Research" 9(15): 3647–3656. The first codon is the codon for the first amino acid found in the mature target protein. Thus, in the case of a target protein expressed in recombinant culture from DNA encoding a secretable preprocessed form of the target protein, the codon at which the chemotactic polypeptide is inserted will be that of the first mature residue and not the amino terminal methionine of the presequence.

Other covalent conjugates are prepared by crosslinking the chemotactic polypeptide to the target. This is accomplished using the same methods and agents as are routinely employed in preparing immunogens from haptens wherein the haptens are bound to immunogenic proteins. Here, the hapten or target protein is bound to the chemotactic polypeptide in place of an immunogenic protein. Suitable crosslinking agents include glutaraldehyde, diazo compounds, succinic anhydride, N-hydroxysuccinimide or m-maleimidobenzoyl sulfosuccinimide ester. Preferably the chemotactic polypeptide is covalently bound to target proteins by a bond which is slightly hydrolysable under physiological conditions, e.g. an ester or disulfide bond.

The chemotactic polypeptides are preferably derived from microorganisms, although chemoattractants from higher organisms, e.g. complement components C5a, are useful. Examples include f-Met-Leu-Phe, f-Met-Met-Met, f-Met-Phe and f-Met-Leu. The preferred polypeptides are f-Met-Leu-Phe-Cys or N-formyl-Nle-Leu-Phe-Nle-Tyr-Lys, and the corresponding crosslinking agents are m-maleimidobenzoyl sulfosuccinimide ester, and N-hydroxysuccinimide or dimethyl subermidate, respectively. Other crosslinking methods and chemotactic polypeptides are referred to in E. Becker et al., "Fed. Proceedings" 39(12): 2949–2950 (1980) except that the chemotactic peptides herein are unlabelled and are not crosslinked to human neutrophil cell surface receptors for such peptides.

Finally, chemotactic polypeptides are simply adsorbed to or entrapped within target proteins or aggregates thereof. For example, aggregates are produced by glutaraldehyde crosslinking in the presence of f-Met-Leu-Phe, whereby the chemotactic tripeptide is entrapped. The availability of the noncovalent adsorption mechanism will depend upon the target protein and will have to be determined by routine screening in which solutions of the protein and labelled chemotactic polypeptides are incubated, the protein removed from solution by preinsolubilization or immune precipitation and the bound or unbound label determined. Systems in which the bound label is maximized are preferred for use in this embodiment.

The anticipated immunogenicity of the conjugates is determined as described herein using the chemotaxis assay. This enables selection of the most potent immunogenic conjugates.

EXAMPLE 1

A membrane granulocyte chemotaxis assay (the complete chemotaxis kit, Neuroprobe, Cabin John, Md.) was used to determine the chemotactic activity of various compositions having or lacking known immunogenic activity, at least based on clinical studies to date. The kit manufacturer's instructions were followed and various concentrations of test compositions were used as shown in the following tables of results. The origin of the test compositions and their known primate or human immunogenicity, if any, are shown in the table. Chemotactic activity is reported as the total number of granulocytes observed in five fields of the kit membrane under 100X magnification. Therefore, the larger the number, the more chemotactic was a composition.

TABLE 1

| Test Sample | | Chemotactic Activity | Immunogenicity |
|---|---|---|---|
| HBSS[1] | | 19 | negative control |
| FMLP | $10^{-6}$ M | 109 | positive control |
| | $10^{-7}$ M | 120 | positive control |
| rhGH[2] lot 11003 | $10^{-6}$ M | 146 | ++ |
| | $10^{-7}$ M | 50 | ++ |
| rhGH lot 11008 | $10^{-6}$ M | 97 | ++ |
| | $10^{-7}$ M | 52 | ++ |
| rhGH lot 11015 | $10^{-6}$ M | 110 | ++ |
| | $10^{-7}$ M | 49 | ++ |
| met-less rhGH[3] | $10^{-6}$ M | 40 | ND |
| | $10^{-7}$ M | 51 | ND |
| hGH[4] | $10^{-6}$ M | 54 | – |
| | $10^{-7}$ M | 27 | – |

[1]Hank's balanced salt solution.
[2]recombinant hGH having amino-terminal methionyl.
[3]recombinant hGH not having an amino terminal methionyl.
[4]hGH recovered from cadaver pituitaries (Crescormon brand of hGH, Kabi Vitrum).
ND not done.

The chemotactic activity of the rhGH preparations appeared to correlate more with their purity rather than the presence or absence of amino terminal methionyl.

Further experiments were conducted on more lots of recombinant hGH which had been purified or processed in various ways (hGH-1 to hGH-9), and cadaver-derived hGH (hGH-10 to hGH-12). The results are shown in Table 2.

TABLE 2

| Test Sample (Concentration) | | Chemotactic Activity | In Vivo Antibody Generation[1] |
|---|---|---|---|
| HBSS | | 6 | |
| FMLP | ($10^{-6}$ M) | 296 | ND |
| FMLP | ($10^{-7}$ M) | 128 | |
| hGH-1 | ($10^{-6}$ M) | 102 | ND |
| | ($10^{-7}$ M) | 42 | |
| hGH-2 | ($10^{-6}$ M) | 18 | 5/6 (no |
| | ($10^{-7}$ M) | 9 | correlation) |
| hGH-3 | ($10^{-6}$ M) | 65 | 4/6 |
| | ($10^{-7}$ M) | 14 | |
| hGH-4 | ($10^{-6}$ M) | 33 | 6/6 (no |
| | ($10^{-7}$ M) | 16 | correlation) |
| hGH-5 | ($10^{-6}$ M) | 91 | ND |
| | ($10^{-7}$ M) | 5 | |
| hGH-6[2] | ($10^{-6}$ M) | 11 | ND |
| | ($10^{-7}$ M) | 6 | |
| hGH-7 | ($10^{-6}$ M) | 62 | 0/6; 5/6 (with |
| | ($10^{-7}$ M) | 10 | high dose) |
| hGH-8 | ($10^{-6}$ M) | 42 | 4/6 |
| | ($10^{-7}$ M) | 21 | |
| hGH-9 | ($10^{-6}$ M) | 79 | 0/6; 5/6 (with |
| | ($10^{-7}$ M) | 14 | high dose) |
| hGH-10 | ($10^{-6}$ M) | 34 | ND |
| | ($10^{-7}$ M) | 6 | |
| hGH-11 | ($10^{-6}$ M) | 8 | 0/6 |
| | ($10^{-7}$ M) | 3 | |
| hGH-12 | ($10^{-6}$ M) | 10 | 2/18 |

TABLE 2-continued

| Test Sample (Concentration) | Chemotactic Activity | In Vivo Antibody Generation[1] |
|---|---|---|
| ($10^{-7}$ M) | 7 | |

[1]Given as the ratio of monkeys that raised anti-hGH antibodies to the total number of animals tested.
[2]Placebo (Mannitol phosphate).
ND: not done.

The recombinant hGH lots were all met-hGH. The immunogenicity of lots hGH-2 and hGH-4 showed no correlation with chemotactic activity at $10^{-6}$ and $10^{-7}$M. However, when the experiments were repeated at concentrations of $1\times10^{-5}$ and $5\times10^{-5}$M a positive correlation was found as shown below in Table 3.

TABLE 3

| Test Sample (Concentration) | | Chemotactic Activity |
|---|---|---|
| HBSS | | 0.0 |
| FMLP | ($10^{-6}$ M) | 196.0 |
| | ($10^{-7}$ M) | 83.0 |
| hGH-2 | ($10^{-5}$ M) | 56.0 |
| | ($5\times10^{-5}$ M) | 10.0 |
| | ($10^{-6}$ M) | 1.0 |
| | ($5\times10^{-6}$ M) | 0.0 |
| | ($10^{-7}$ M) | 1.0 |
| hGH-3 | ($10^{-5}$ M) | 130.0 |
| | ($5\times10^{-5}$ M) | 20.0 |
| | ($10^{-6}$ M) | 6.0 |
| | ($5\times10^{-6}$ M) | 0.0 |
| | ($10^{-7}$ M) | 0.0 |
| hGH-4 | ($10^{-5}$ M) | 33.0 |
| | ($5\times10^{-5}$ M) | 8.0 |
| | ($10^{-6}$ M) | 4.0 |
| | ($5\times10^{-6}$ M) | 1.0 |
| | ($10^{-7}$ M) | 0.0 |
| hGH[1] | ($10^{-5}$ M) | 10.0 |
| | ($5\times10^{-5}$ M) | 15.0 |
| | ($10^{-6}$ M) | 7.0 |
| | ($5\times10^{-6}$ M) | 1.0 |
| | ($10^{-7}$ M) | 1.0 |

[1]Crescormon brand of cadaver hGH.

Finally, experiments were conducted to determine the effect of other recombinant protein compositions in the chemotaxis assay. Bovine alpha and gamma interferon (Bo-alpha and Bo-Gamma), and a clinical grade lot of human gamma interferon (Genentech, Inc., lot G11023-01, HuIFN-gamma) were compared with cadaver hGH (Kabi Vitrum) in the chemotaxis assay. This human gamma interferon is not immunogenic in vivo. The results are shown in Table 4.

TABLE 4

| Test Sample (Concentration) | | Chemotactic Activity |
|---|---|---|
| HBSS | | 2 |
| FMLP | ($10^{-6}$ M) | 212 |
| | ($10^{-7}$ M) | 165 |
| hGH[1] | ($10^{-6}$ M) | 24 |
| | ($10^{-7}$ M) | 12 |
| rBo Alpha | ($10^{-6}$ M) | 11 |
| | ($10^{-7}$ M) | 4 |
| rBo Gamma | ($10^{-6}$ M) | 1 |
| | ($10^{-7}$ M) | 6 |
| rHuIFN-Gamma | ($10^{-6}$ M) | 4 |
| | ($10^{-7}$ M) | 1 |

[1]Crescormon brand of cadaver hGH

EXAMPLE 2

Recombinant Preparation of a Fusion Between a Chemotactic Polypeptide and Target Protein This example in concerned with the preparation of an immunogenic conjugate of f-Met-Leu-Phe and the foot and mouth disease VP3 gene. DNA fragment 4a of European Patent Application 68,693 is prepared as described except that the synthetic oligonucleotides are as follows: AATTCATGCT, GTTCACTACT, GCTACTGGTG, AATCTGCAGA, TTCACCAGTA and GCAGTAGTCATG. The oligonucleotides are incorporated into an expression vector and used to transform E. coli K12 strain 294 as described in EP 68,693A. The transformants synthesize a VP3 fusion protein having the N-terminal sequence f-Met-Leu-Phe-Thr-Thr-Ala-Thr, wherein the Leu and Phe residues are inserted between residues 1 and 2 of VP3. This fusion is recovered from cell culture and used to immunize cattle as provided in EP 68,693A.

I claim:

1. A method for determining the likelihood that a composition containing a protein made in recombinant culture will be immunogenic in recipients, comprising contacting leukocytes with the composition, and observing for chemotactic effect of the composition.

2. The method of claim 1 wherein the leukocytes are human neutrophils and the protein is a human protein.

3. The method of claim 1 wherein the chemotactic effect observed is the migration of the leukocytes towards higher concentrations of the composition.

4. The method of claim 1 wherein the recombinant culture is a bacterial, yeast or vertebrate cell culture.

5. The method of claim 1 wherein the chemotactic effect is measured by the production of superoxide anion by the leukocytes.

6. The method of claim 1 wherein the chemotactic effect is measured by the secretion of lysosomal enzymes by the leukocytes.

7. The method of claim 6 wherein the lysosomal enzyme is N-acetyl-$\beta$-D-glucosaminidase.

8. The method of claim 1 wherein the protein is contacted with the leukocytes by allowing a solution of the protein to diffuse across a membrane into contact with the leukocytes.

9. The method of claim 8 wherein the protein is present in the solution at a concentration ranging about from $1\times10^{-5}$M to $1\times10^{-8}$M.

10. A method comprising (a) synthesizing a protein in recombinant cell culture, (b) processing the protein into a candidate therapeutic composition, (c) contacting leukocytes with the composition, (d) observing for chemotactic effect of the composition on the leukocytes, (e) when the composition is chemotactic then modifying steps (a) or (b) to reduce or increase the chemotactic effect of the composition, (f) contacting leukocytes with a composition made by the modified steps (a) or (b) and (g) observing for chemotactic effect of the step (f) composition on the leukocytes of step (f).

11. The method of claim 10 wherein the leukocytes are human neutrophils.

12. The method of claim 10 the chemotactic effect observed is the migration of the leukocytes towards higher concentrations of the composition.

13. The method of claim 10 wherein the recombinant culture is a bacterial, yeast or vertebrate cell culture.

14. The method of claim 10 wherein the composition is chemotactic if it exhibits greater than about 10 percent of the chemotactic activity of f-Met-Leu-Phe.

15. The method of claim 10 wherein steps (a) or (b) are modified to reduce the chemotactic effect of the composition.

16. The method of claim 10 wherein the leukocytes are a mixture of motile leukocyte cell types.

17. The method of claim 10 wherein step (b) is modified to reduce or increase the chemotactic effect of the composition.

18. The method of claim 10 wherein the protein is contacted with the leukocytes by allowing a solution of the protein to diffuse across a membrane into contact with the leukocytes.

19. The method of claim 17 wherein the protein is present in the solution at a concentration ranging about from $1 \times 10^{-5}$M to $1 \times 10^{-8}$M.

20. The method of claim 10 wherein the processing of step (b) includes a purification procedure for recovering the protein from the cell culture.

21. The method of claim 20 wherein the purification procedure is modified to reduce or increase the chemotatic effect of the composition.

22. The method of claim 10 where step (a) is modified to reduce the chemotactic effect of the composition.

23. The method of claim 22 wherein the recombinant cell culture is modified to synthesize a mature rather than methionyl amino-terminal protein.

24. The method of claim 22 wherein the amino acid sequence of the protein is modified.

25. The method of claim 22 wherein the host cell used in step (a) is substituted by another host cell.